United States Patent
Heni et al.

(10) Patent No.: US 10,477,190 B2
(45) Date of Patent: Nov. 12, 2019

(54) CONSTANT HORIZON 3D IMAGING SYSTEM AND RELATED METHOD

(71) Applicants: Karl Storz SE & Co. KG, Tuttlingen (DE); Karl Storz Imaging, Inc., Goleta, CA (US)

(72) Inventors: Andreas Heni, Fridingen (DE); Markus Kupferschmid, Emmingen-Liptingen (DE); Daniel Ulmschneider, Nendingen (DE); Lawrence Natusch, Tuttlingen (DE); George E. Duckett, III, Castaic, CA (US)

(73) Assignees: Karl Storz Imaging, Inc., Goleta, CA (US); Karl Storz SE & Co. KG, Tuttlingen (DE)

(*) Notice: Subject to any disclaimer, the term of this patent is extended or adjusted under 35 U.S.C. 154(b) by 172 days.

(21) Appl. No.: 15/458,199

(22) Filed: Mar. 14, 2017

(65) Prior Publication Data
US 2018/0270466 A1    Sep. 20, 2018

(51) Int. Cl.
*H04N 13/296* (2018.01)
*G02B 23/24* (2006.01)
(Continued)

(52) U.S. Cl.
CPC ....... *H04N 13/296* (2018.05); *A61B 1/00179* (2013.01); *A61B 1/00193* (2013.01);
(Continued)

(58) Field of Classification Search
CPC ..... A61B 1/005; A61B 1/008; A61B 1/00193; A61B 1/0009
See application file for complete search history.

(56) References Cited

U.S. PATENT DOCUMENTS

| 4,862,873 A | 9/1989 | Yajima et al. |
| 5,976,071 A * | 11/1999 | Sekiya ............... A61B 1/00193 600/111 |

(Continued)

FOREIGN PATENT DOCUMENTS

| DE | 10050351 A1 | 5/2001 |
| DE | 102008030349 A1 | 1/2009 |

(Continued)

OTHER PUBLICATIONS

European Search Report, Application No. EP18161221, completed: Jul. 11, 2018;dated Jul. 26, 2018, 7 pages.

*Primary Examiner* — Pankaj Kumar
*Assistant Examiner* — Timothy R Newlin
(74) *Attorney, Agent, or Firm* — Whitmyer IP Group LLC

(57) ABSTRACT

An imaging system includes an imaging scope, a controller, a camera, and a processor. The imaging scope is selectively rotatable about a longitudinal axis relative to a horizon plane. The imaging scope has at least three optical channels, each including a respective objective that captures light. The objectives are positioned such that respective viewing direction axes of the optical channels extend at least substantially parallel to one another. The controller activates a pair of optical channels that is at least as parallel relative to the horizon plane as any other pair of optical channels. The camera generates a first image representative of light captured by a first optical channel of the activated pair of optical channels, and a second image representative of light captured by a second optical channel of the activated pair of optical channels. The processor generates a 3D image using the first and second images.

26 Claims, 10 Drawing Sheets

(51) Int. Cl.
*H04N 13/189* (2018.01)
*H04N 13/243* (2018.01)
*A61B 1/00* (2006.01)
*H04N 13/239* (2018.01)

(52) U.S. Cl.
CPC ..... *G02B 23/2415* (2013.01); *G02B 23/2423* (2013.01); *G02B 23/2484* (2013.01); *H04N 13/189* (2018.05); *H04N 13/243* (2018.05); *H04N 13/239* (2018.05)

(56) References Cited

U.S. PATENT DOCUMENTS

| | | | |
|---|---|---|---|
| 6,139,490 A * | 10/2000 | Breidenthal | A61B 1/00193 600/111 |
| 6,522,906 B1 * | 2/2003 | Salisbury, Jr. | A61B 1/313 600/102 |
| 6,767,321 B2 | 7/2004 | Czarnek et al. | |
| 7,372,642 B2 | 5/2008 | Rohaly et al. | |
| 8,911,358 B2 | 12/2014 | Koninckx et al. | |
| 8,928,746 B1 | 1/2015 | Stevrin et al. | |
| 9,068,824 B2 * | 6/2015 | Findeisen | A61B 1/00096 |
| 9,835,564 B2 * | 12/2017 | Olsson | A61B 1/05 |
| 2002/0035310 A1 * | 3/2002 | Akui | A61B 1/00183 600/111 |
| 2002/0114071 A1 | 8/2002 | Igarashi | |
| 2004/0249246 A1 * | 12/2004 | Campos | A61B 1/0008 600/160 |
| 2008/0027279 A1 * | 1/2008 | Abou El Kheir | A61B 1/0008 600/111 |
| 2008/0151041 A1 * | 6/2008 | Shafer | A61B 1/00193 348/45 |
| 2010/0245549 A1 * | 9/2010 | Allen | A61B 1/00183 348/65 |
| 2010/0274089 A1 * | 10/2010 | Choi | A61B 1/00071 600/166 |
| 2011/0057930 A1 | 3/2011 | Keller et al. | |
| 2011/0306832 A1 * | 12/2011 | Bassan | A61B 1/00009 600/109 |
| 2013/0085329 A1 * | 4/2013 | Morrissette | A61B 1/00193 600/111 |
| 2013/0162776 A1 * | 6/2013 | Noack | A61B 1/0008 348/45 |
| 2014/0293007 A1 | 10/2014 | Angot et al. | |
| 2015/0062299 A1 | 3/2015 | Brown et al. | |

FOREIGN PATENT DOCUMENTS

| | | |
|---|---|---|
| DE | 102008024732 A1 | 1/2010 |
| DE | 102010064387 A1 | 7/2012 |
| DE | 102011100997 A1 | 11/2012 |
| DE | 102013208306 A1 | 11/2014 |
| DE | 102014107432 B3 | 6/2015 |
| WO | 2012041445 A1 | 4/2012 |

* cited by examiner

CONSTANT HORIZON 3D IMAGING SYSTEM AND RELATED METHOD

TECHNICAL FIELD

The present disclosure generally relates to an imaging system and a related method. The present disclosure more particularly relates to a constant horizon three-dimensional (3D) imaging system and a related method that involves an imaging scope (e.g., an endoscope, an exoscope, a borescope, etc.) and a camera.

BACKGROUND

It is known to provide an imaging system having an imaging scope (e.g., an endoscope, an exoscope, a borescope, etc.) that captures light reflected from an object, and a camera that converts the captured light into digital images. It is also known to provide 3D imaging systems that are capable of generating 3D digital images. In such 3D imaging systems, the imaging scope includes two separate optical channels that define a separation distance therebetween and are positionally-fixed relative to the imaging scope. The camera generates a first two-dimensional (2D) digital image representative of light captured by the first optical channel and a second 2D digital image representative of light captured by the second optical channel. The 3D digital image is generated by combining at least portions of the first 2D digital image and the second 2D digital image.

Such 3D imaging systems can be problematic in that, during rotation of the imaging scope relative to a real-world horizon plane (e.g., a plane perpendicular to a gravity vector), the 3D digital image displayed on the monitor shows a corresponding rotation. That is, the horizon of the 3D digital image displayed on the monitor will no longer correspond to the real-world horizon plane. As the imaging scope is rotated, it is impossible to maintain a 3D digital image, in particular a 3D digital image having a horizon that is aligned with the real-world horizon plane. The separation of the two optical channels in a direction parallel to the real-world horizon plane gets smaller and smaller, and disappears completely when the imaging scope is rotated ninety degrees (90°) about a longitudinal axis of the imaging scope, thus making it impossible for a user to view a 3D digital image.

Aspects of the present invention are directed to these and other problems.

SUMMARY

According to an aspect of the present invention, an imaging system includes an imaging scope, a controller, a camera, and a 3D processor. The imaging scope extends along a longitudinal axis between a proximal end portion and a distal end portion thereof. The imaging scope is selectively rotatable about the longitudinal axis relative to a horizon plane. The imaging scope has at least three optical channels, each including a respective objective positioned at the distal end portion of the imaging scope, and each configured to capture light reflected from an object. The objectives of the at least three optical channels are annularly-spaced relative to one another and positioned such that respective viewing direction axes of the at least three optical channels extend at least substantially parallel to one another. The controller is configured to activate, among the at least three optical channels, a pair of optical channels that is at least as parallel relative to the horizon plane as any other pair of optical channels among the at least three optical channels. The camera is configured to generate a first 2D digital image representative of light captured by a first optical channel of the activated pair of optical channels, and a second 2D digital image representative of light captured by a second optical channel of the activated pair of optical channels. The 3D processor is configured to generate a 3D digital image using the first 2D digital image and the second 2D digital image.

According to another aspect of the present invention, an imaging system includes an imaging scope, a controller, a camera, and a 3D processor. The imaging scope extends along a longitudinal axis between a proximal end portion and a distal end portion thereof. The imaging scope is selectively rotatable about the longitudinal axis relative to a horizon plane. The imaging scope has at least three optical channels, each including a respective objective positioned at the distal end portion of the imaging scope, and each configured to capture light reflected from an object. The objectives of the at least three optical channels are annularly-spaced relative to one another and positioned such that respective viewing direction axes of the at least three optical channels extend at least substantially parallel to one another. The controller is configured to activate, among the at least three optical channels, a pair of optical channels defining a viewing horizon line that is at least as parallel relative to the horizon plane as that of any other pair of optical channels among the at least three optical channels. The viewing horizon line is a line that extends perpendicularly between the respective viewing direction axes of the pair of optical channels. The camera is configured to generate a first 2D digital image representative of light captured by a first optical channel of the activated pair of optical channels, and a second 2D digital image representative of light captured by a second optical channel of the activated pair of optical channels. The 3D processor is configured to generate a 3D digital image using the first 2D digital image and the second 2D digital image.

According to another aspect of the present invention, a method comprising: (i) providing an imaging scope that extends along a longitudinal axis between a proximal end portion and a distal end portion thereof, the imaging scope having at least three optical channels, each including a respective objective positioned at the distal end portion of the imaging scope, and each configured to capture light reflected from an object, the objectives being annularly-spaced relative to one another and positioned such that respective viewing direction axes of the at least three optical channels extend at least substantially parallel to one another; (ii) rotating the imaging scope about the longitudinal axis relative to a horizon plane; (iii) activating, among the at least three optical channels, a pair of optical channels that is at least as parallel relative to the horizon plane as any other pair of optical channels among the at least three optical channels; (iv) generating a first 2D digital image representative of light captured by a first optical channel of the activated pair of optical channels, and a second 2D digital image representative of light captured by a second optical channel of the activated pair of optical channels; and (v) generating a 3D digital image using the first 2D digital image and the second 2D digital image.

In addition to, or as an alternative to, one or more of the features described above, further aspects of the present invention can include one or more of the following features, individually or in combination:

the horizon plane is an imaginary plane that is oriented perpendicular relative to a gravity vector;

the horizon plane is oriented parallel relative to a gravity vector;

the horizon plane is non-perpendicularly offset relative to the gravity vector;

the horizon plane is selectively chosen and adjusted by a user;

the imaging scope further includes a shaft, a housing, and a window;

the shaft extends along (i.e., extends in a direction of) the longitudinal axis of the imaging scope;

the shaft is rigid and includes a tubular shaft wall and a shaft channel defined by an inner surface of the shaft wall;

the outer surface of the shaft wall defines a diameter of approximately four millimeters (4 mm), five millimeters (5 mm), ten millimeters (10 mm), and/or another magnitude;

the housing is integrally connected to the proximal end portion of the shaft;

the housing serves as a handle of the imaging scope that can be grasped by a user during use of the imaging scope;

the housing is releasably connected to the proximal end portion of the shaft;

the housing is not intended to serve as a handle of the imaging scope;

the window is disposed at the distal end portion of the shaft, and is made of glass or another suitable material that is at least substantially transparent;

the window is planar and is non-perpendicularly offset relative to the longitudinal axis of the imaging scope;

multiple windows are disposed at the distal end portion of the shaft;

multiple windows disposed at the distal end portion of the shaft are arranged such that they all lie in a common plane;

multiple windows disposed at the distal end portion of the shaft are arranged such that each lies in a different respective plane;

one or more windows disposed at the distal end portion of the shaft are oriented perpendicular relative to the longitudinal axis of the imaging scope;

one or more windows disposed at the distal end portion of the shaft have a spherical or other non-planar shape;

the housing of the imaging scope houses the camera, the controller, and the 3D processor;

at least one of the camera, the controller, and the 3D processor are housed within the shaft of the imaging scope;

the camera is housed in the distal end portion of the shaft of the imaging scope, while the controller and the 3D processor are housed in the housing of the imaging scope;

at least one of the camera, the controller, and the 3D processor are remotely positioned relative to the imaging scope;

the housing houses at least the camera, and the housing is characterized as a camera housing;

the housing houses at least the camera, and the housing is characterized as a camera head;

each of the at least three optical channels includes a respective objective positioned at the distal end portion of the imaging scope;

each of the objectives has a field of view, and a light entrance surface that captures light reflected from an object and passed through the window;

the viewing direction axes of the optical channels are angularly offset relative to the longitudinal axis of the imaging scope (e.g., by thirty degrees (30°), forty-five degrees (45°), sixty degrees (60°), or another magnitude);

the viewing direction axes each extend perpendicular to the light entrance surface of the objective of the respective optical channel;

the orientations of the viewing direction axes vary as the imaging scope is rotated about its longitudinal axis;

the imaging scope has an "oblique viewing" configuration and/or a "side viewing" configuration;

the viewing direction axes are oriented parallel relative to the longitudinal axis of the imaging scope;

the imaging scope has an "end viewing" configuration and/or an angular offset of zero degrees (0°);

each of the at least three optical channels further includes a respective image transmission device that transmits the captured light from the respective objectives of the optical channels to the camera;

each image transmission device includes a rod lens, and each transmits the captured light therethrough in the form of a captured light beam having a circular cross-sectional shape;

the image transmission devices are configured to transmit the captured light therethrough in the form of a captured light beam having another cross-sectional shape that is at least partially circular (e.g., ovular, elliptical, etc.);

the imaging scope includes three (3) optical channels, four (4) optical channels, five (5) optical channels, six (6) optical channels, or more than six (6) optical channels;

the imaging scope includes a plurality of light sources positioned within the shaft channel proximate the window;

the light sources are positioned radially between the optical channels and the shaft wall;

the light sources are connected to the controller via wires;

the controller controls (e.g., activates, deactivates) the light sources such that the light sources selectively illuminate an object by selectively emitting illumination light through the window and out of the distal end of the imaging scope;

the controller is configured to selectively activate one or more light sources depending on which optical channels form the activated pair;

the controller is configured to continuously change which light sources are activated in order to keep up with continuous changes to which optical channels form the activated pair;

the camera includes at least two image sensors;

each of the image sensors includes at least a portion of a light-sensitive surface configured to receive captured light from one of the optical channels of the imaging scope, and each is configured to generate a 2D digital image representative of such captured light;

a single component forms more than one image sensor;

the light sensitive surface of a CCD or another imaging device is subdivided into several predetermined portions, with each of the several predetermined portions forming a separate image sensor;

the number of image sensors is the same as the number of optical channels of the imaging scope;

the camera includes only two (2) image sensors, or another number of image sensors that is fewer than the number of optical channels of the imaging scope;

the image sensors are positionally fixed relative to the optical channels during operation of the imaging system;

each of the optical channels is permanently paired with a respective image sensor;

the image sensors are rotatable relative to the optical channels during operation of the imaging system;

a parallel alignment of the two (2) image sensors relative to the horizon plane remains fixed during operation of the imaging system;

the camera is a video camera, and the 2D digital images generated by the image sensors represent one of a plurality of time-sequenced frames of a digital video;

the controller is in signal communication with the camera (in particular, the image sensors of the camera);

during activation of an optical channel, the controller causes the optical channel to be one from which captured light is used by the camera to generate the 2D digital images;

light captured and transmitted through an activated optical channel is subsequently received by the light-sensitive surface of an image sensor of the camera, and the respective image sensor generates a 2D digital image representative thereof;

light captured and transmitted through an optical channel that has not been activated by the controller will not be received by an image sensor of the camera;

the image sensor will not generate a 2D digital image representative of light captured and transmitted through an optical channel that has not been activated by the controller;

the image sensor will generate a 2D digital image representative of light captured and transmitted through an optical channel that has not been activated by the controller, but the 3D processor will not use that 2D digital image to generate a 3D digital image;

the controller activates a particular optical channel by instructing a corresponding image sensor of the camera to generate a 2D digital image representative of the light received from the particular optical channel;

the controller activates a particular pair of optical channels by sending instructions to the camera that causes movement of the image sensors relative to the optical channels until the image sensors are aligned with the particular pair of optical channels;

a gravity sensor sends a data signal to the controller regarding the orientation and/or movement of the imaging scope relative to the direction of a gravity vector, and the controller uses such data to activate a pair of optical channels;

the horizon plane is chosen and/or determined by the controller based on the data signal received from the gravity sensor;

the gravity sensor is positioned within the housing of the imaging scope;

the gravity sensor is positioned within the shaft of the imaging scope, or in another location where the gravity sensor will be rotated together with the imaging scope and/or the optical channels thereof;

the gravity sensor is in the form of a three-axis acceleration sensor;

the gravity sensor is configured to be turned off manually and the orientation of the horizon plane selectively chosen and adjusted by a user;

additional sensors like magnetometers and gyroscopes are used to improve or correct the measurement of such a gravity sensor;

the controller is configured to perform known digital image erecting and digital flip-mirror functions on the 2D digital images before transmitting the same to the 3D processor;

the functionality of the controller is implemented using mechanical, analog and/or digital hardware, software, firmware, or a combination thereof;

the controller performs one or more of the functions by executing software, which is stored in a memory device;

the 3D processor is in signal communication with the controller, and receives the 2D digital images from the controller and processes the 2D digital images in a known manner to generate a 3D digital image;

the 3D processor is configured to calculate a depth map using the 2D digital images;

the depth map provides a calculation of the relative distances from the window at the distal end of the imaging scope to various objects across the field of view of the imaging scope;

the parallax between the 2D digital images allows the 3D processor to calculate such a depth map;

the functionality of the 3D processor is implemented using analog and/or digital hardware, software, firmware, or a combination thereof; and the 3D processor performs one or more of the functions by executing software, which is stored in a memory device.

These and other aspects of the present invention will become apparent in light of the drawings and detailed description provided below.

DETAILED DESCRIPTION

Figure 1:
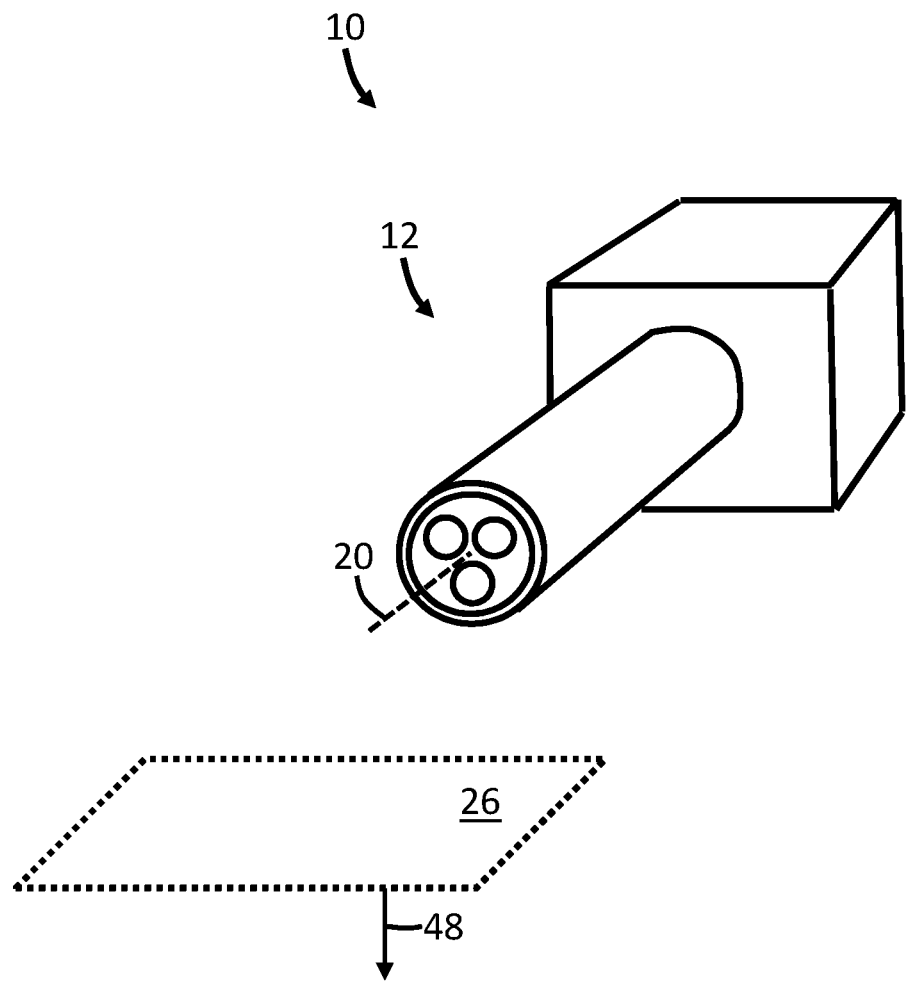
FIG. 1 schematically illustrates an imaging system including an imaging scope, a controller (see FIG. 2), a camera (see FIG. 2), and a 3D processor (see FIG. 2).
Figure 2:
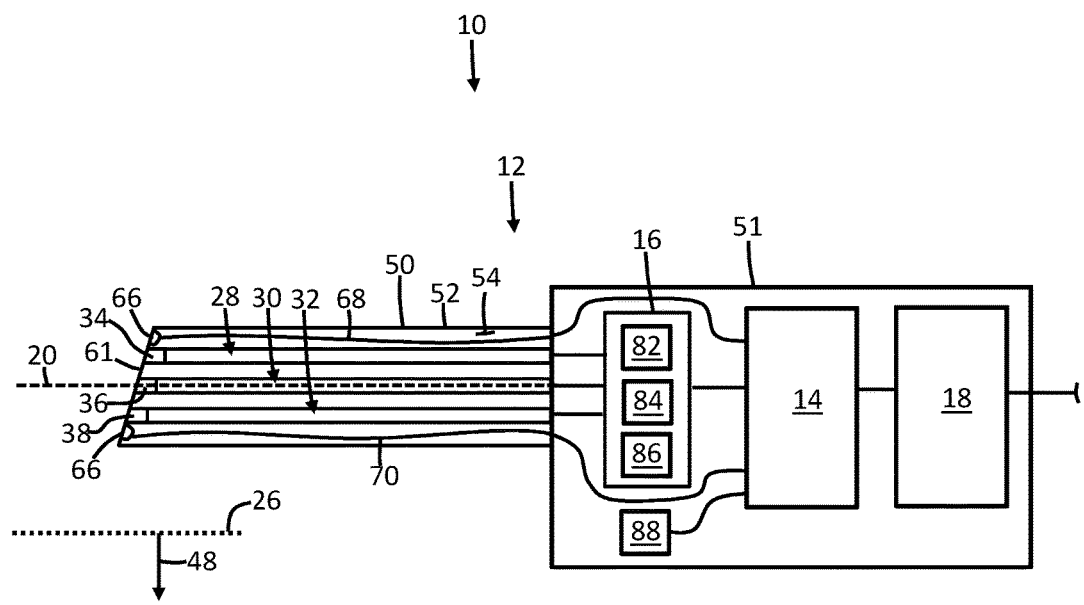
FIG. 2 schematically illustrates the imaging system of FIG. 1.

Referring to FIGS. 1 and 2, the present disclosure describes an imaging system 10 and a related method. The imaging system 10 includes an imaging scope 12, a controller 14 (see FIG. 2), a camera 16 (see FIG. 2), and a 3D processor 18 (see FIG. 2).

Figure 3:
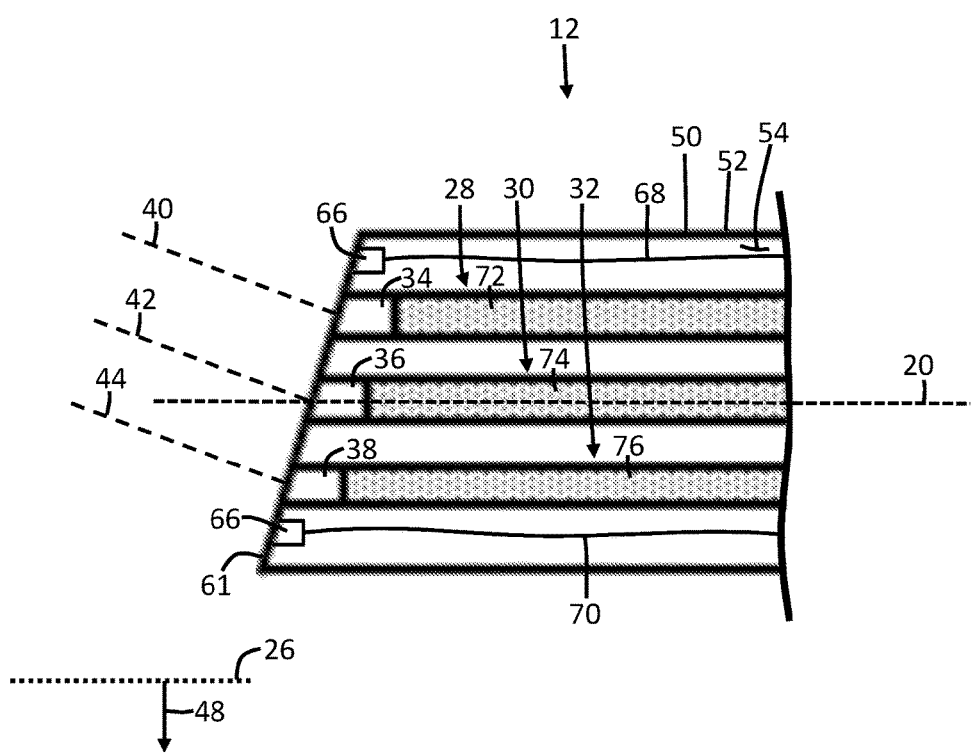
FIG. 3 schematically illustrates a distal end portion of the imaging scope of FIG. 1.

Referring to FIGS. 2 and 3, the imaging scope 12 (e.g., an endoscope, an exoscope, a borescope, etc.) extends along a longitudinal axis 20 between a proximal end portion and a distal end portion thereof. The imaging scope 12 is selectively rotatable about the longitudinal axis 20 relative to a horizon plane 26. The imaging scope 12 has at least three optical channels 28, 30, 32, each including a respective objective 34, 36, 38 (e.g., an objective prism, an objective lens, etc.) positioned at the distal end portion of the imaging scope 12, and each configured to capture light reflected from an object (e.g., an internal body cavity of a patient). The objectives 34, 36, 38 are annularly-spaced relative to one another and are positioned such that their respective viewing direction axes 40, 42, 44 (see FIG. 3) extend at least substantially parallel to one another. The controller 14 (see FIG. 2) is configured to activate, among the at least three optical channels 28, 30, 32, a pair of optical channels that is at least as parallel relative to the horizon plane 26 as any other pair among the at least three optical channels 28, 30, 32. The activated pair of optical channels defines a viewing horizon line 46 (see FIGS. 4, 6, 8) that is at least as parallel relative to the horizon plane 26 as that of any other pair among the at least three optical channels 28, 30, 32. The viewing horizon line 46 is an imaginary line that extends perpendicularly between the respective viewing direction axes 40, 42, 44 (see FIG. 3) of the optical channels included in the activated pair of optical channels. The camera 16 (see FIG. 2) is configured to generate a first 2D digital image representative of light captured by a first optical channel of the activated pair of optical channels, and a second 2D digital image representative of light captured by a second optical channel of the activated pair of optical channels. The 3D processor 18 (see FIG. 2) is configured to generate a 3D digital image using the first 2D digital image and the second 2D digital image. In some embodiments, the imaging system 10 further includes a monitor (not shown) on which the 3D digital image is displayed.

In the embodiment illustrated in FIGS. 1-9, the horizon plane 26 is an imaginary plane that is oriented perpendicular relative to a gravity vector 48. In other embodiments, such as that illustrated in FIG. 10, the horizon plane 26 can be oriented parallel relative to a gravity vector 48. In still other embodiments, the horizon plane can be non-perpendicularly offset relative to the gravity vector 48, and/or the orientation of the horizon plane 26 can be selectively chosen and adjusted by a user (e.g., via an input device on the imaging scope 12).

Referring to FIGS. 2 and 3, the imaging scope 12 further includes a shaft 50, a housing 51, and a window 61.

The shaft 50 extends along (i.e., extends in a direction of) the longitudinal axis 20 of the imaging scope 12. In the illustrated embodiments, the shaft 50 is rigid and includes a tubular shaft wall 52 and a shaft channel 54 defined by an inner surface of the shaft wall 52. The outer surface of the shaft wall 52 defines a diameter (e.g., a diameter of approximately four millimeters (4 mm), five millimeters (5 mm), ten millimeters (10 mm), and/or another magnitude).

In the illustrated embodiments, the housing 51 is integrally connected to the proximal end portion of the shaft 50, and the housing 51 serves as a handle of the imaging scope 12 that can be grasped by a user during use of the imaging scope 12. In some embodiments, the housing 51 is releasably connected to the proximal end portion of the shaft 50, and/or the housing 51 is not intended to serve as a handle of the imaging scope 12.

The window 61 is disposed at the distal end portion of the shaft 50, and is made of glass or another suitable material that is at least substantially transparent. In the illustrated embodiments, the window 61 is planar, and is non-perpendicularly offset relative to the longitudinal axis 20 of the imaging scope 12. In other embodiments, there can be multiple windows disposed at the distal end portion of the shaft 50 (e.g., one window for each of the at least three optical channels 28, 30, 32). The multiple windows can be arranged such that they all lie in a common plane, or such that each window lies in a different respective plane. In some embodiments, the one or more windows can be oriented perpendicular relative to the longitudinal axis 20 of the imaging scope 12, rather than being non-perpendicularly offset relative to the longitudinal axis 20 as shown in the illustrated embodiments. Also, in some embodiments, the one or more windows can each have a spherical or other non-planar shape.

Figure 11:
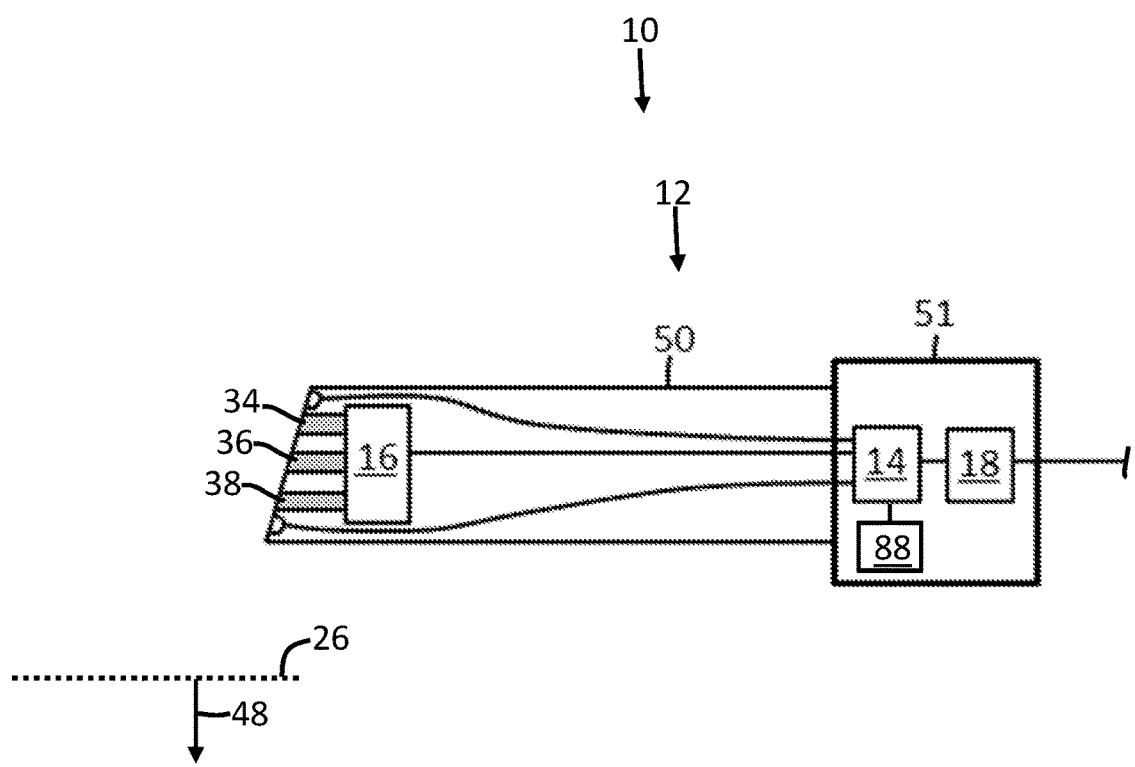
FIG. 11 schematically illustrates another imaging system in which the camera is positioned in the distal end portion of the shaft of the imaging scope.

In the embodiment illustrated in FIGS. 1-9, the housing 51 of the imaging scope 12 houses the camera 16, the controller 14, and the 3D processor 18. In other embodiments, at least one of the camera 16, the controller 14, and the 3D processor 18 can be housed within the shaft 50 of the imaging scope 12. In the embodiment of FIG. 11, for example, the camera 16 is housed in the distal end portion of the shaft 50 of the imaging scope 12, while the controller 14 and the 3D processor 18 are housed in the housing 51 of the imaging scope 12. In some embodiments, at least one of the camera 16, the controller 14, and the 3D processor 18 can be remotely positioned relative to the imaging scope 12. In some embodiments in which the housing 51 houses at least the camera 16, the housing 51 can additionally or alternatively be characterized as a camera housing or a camera head.

Referring to FIGS. 2 and 3, each of the at least three optical channels 28, 30, 32 includes a respective objective 34, 36, 38 positioned at the distal end portion of the imaging scope 12 (e.g., at the distal end portion of the shaft 50). In the illustrated embodiments, each of the objectives 34, 36, 38 has a field of view, and a light entrance surface that captures light reflected from an object and passed through the window 61. The viewing direction axes 40, 42, 44 of the optical channels 28, 30, 32 are angularly offset relative to the longitudinal axis 20 of the imaging scope 12 (e.g., angularly offset by thirty degrees (30°), forty-five degrees (45°), sixty degrees (60°), or another magnitude). The viewing direction axes 40, 42, 44 each extend perpendicular to the light entrance surface of the objective 34, 36, 38 of the respective optical channel 28, 30, 32. Due to the angular offset of the viewing direction axes 40, 42, 44 relative to the longitudinal axis 20 of the imaging scope 12, the orientations of the viewing direction axes 40, 42, 44 vary as the imaging scope 12 is rotated about its longitudinal axis 20. The imaging scope 12 can thus be said to have an "oblique viewing" configuration and/or a "side viewing" configuration. In other embodiments, the viewing direction axes 40, 42, 44 can be oriented parallel relative to the longitudinal axis 20 of the imaging scope 12. In such embodiments, the imaging scope 12 can be said to have an "end viewing" configuration and/or an angular offset of zero degrees (0°).

Figure 4:
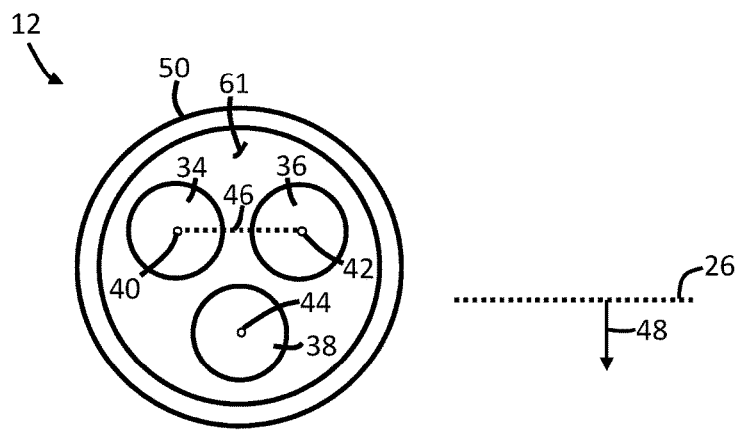
FIG. 4 schematically illustrates the distal end of the imaging scope of FIG. 1 in a first rotational position.
Figure 5:
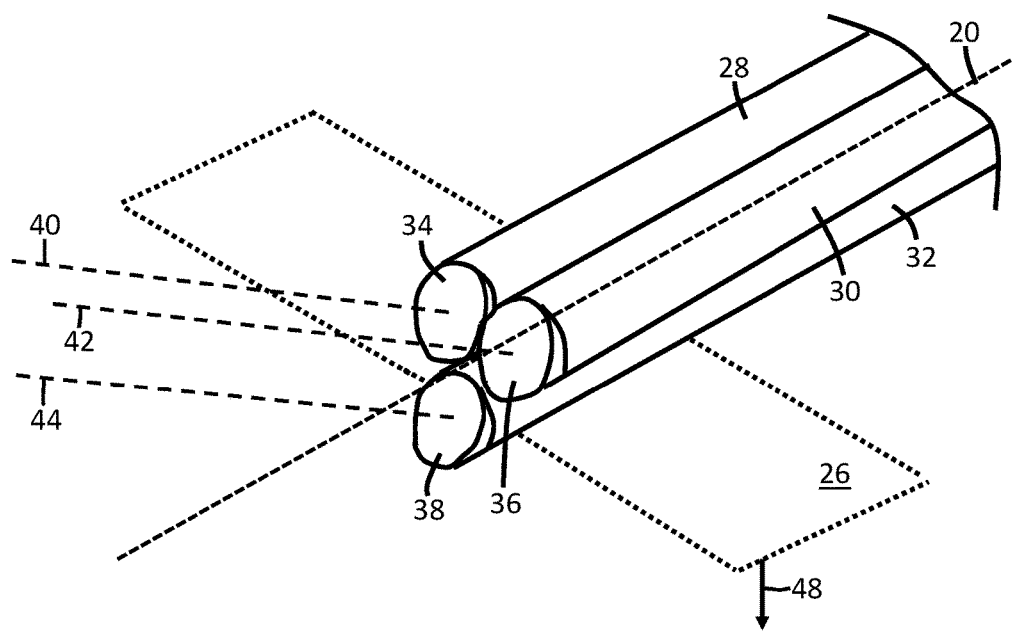
FIG. 5 schematically illustrates portions of the imaging scope of FIG. 1 in the first rotational position.
Figure 6:
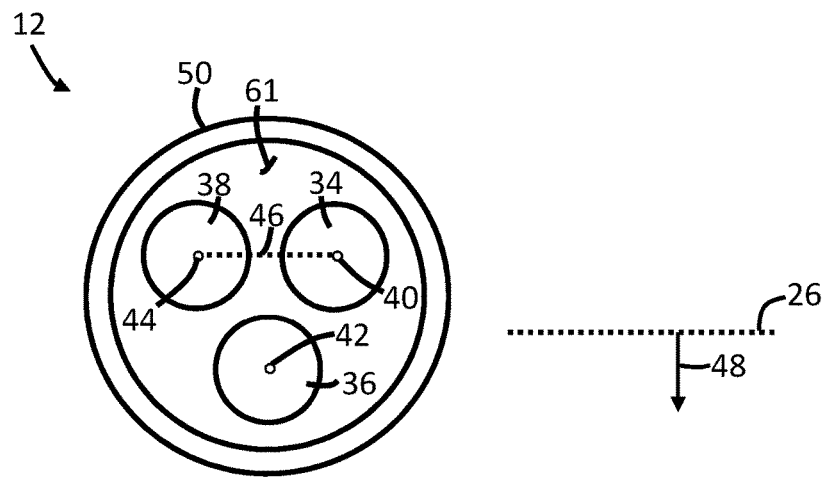
FIG. 6 schematically illustrates the distal end of the imaging scope of FIG. 1 in a second rotational position.
Figure 7:
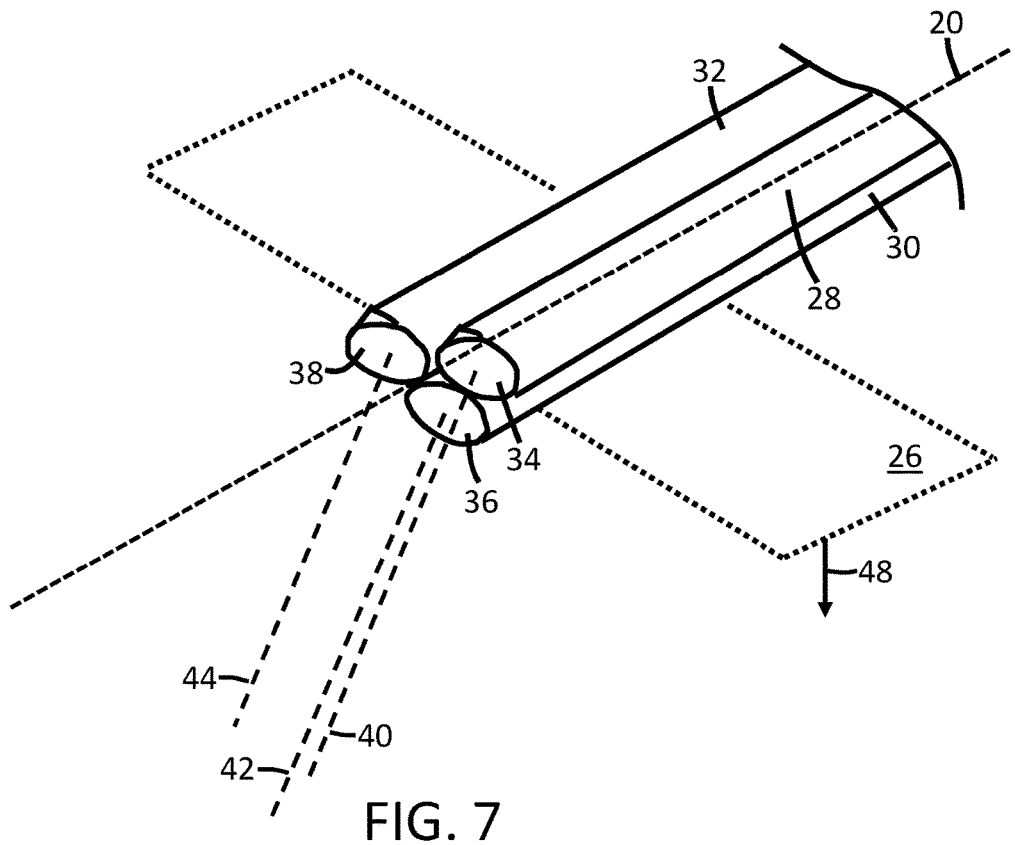
FIG. 7 schematically illustrates portions of the imaging scope of FIG. 1 in the second rotational position.
Figure 8:
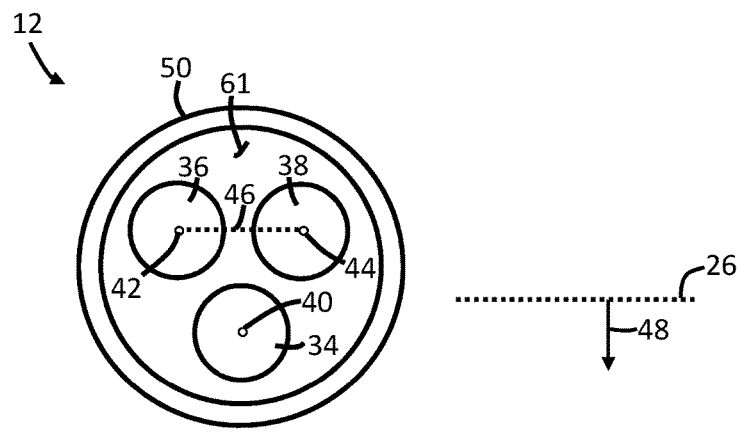
FIG. 8 schematically illustrates the distal end of the imaging scope of FIG. 1 in a third rotational position.
Figure 9:
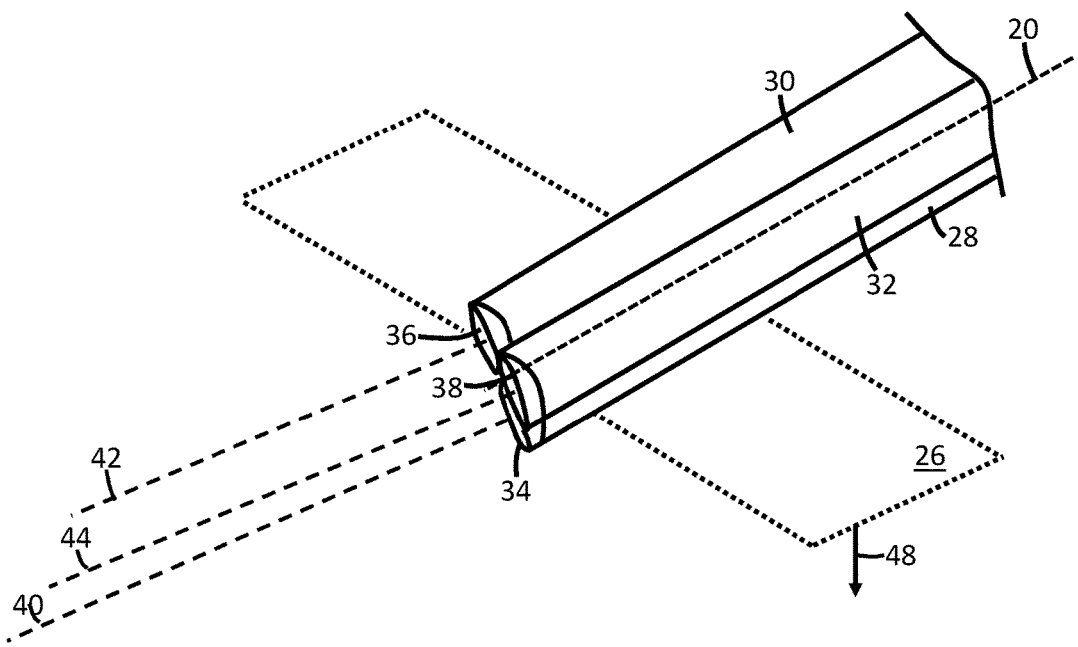
FIG. 9 schematically illustrates portions of the imaging scope of FIG. 1 in the third rotational position.

FIG. 4 illustrates the distal end of the imaging scope 12 of FIGS. 1-3 when the imaging scope 12 is in a first position, and FIG. 5 illustrates the orientations of the viewing direction axes 40, 42, 44 of the optical channels 28, 30, 32 when the imaging scope 12 is in the first position. FIG. 6 illustrates the distal end of the imaging scope 12 when the imaging scope 12 is in a second position in which the imaging scope 12 has been rotated about its longitudinal axis 20 by one hundred twenty degrees (120°) compared to the first position (see FIGS. 4 and 5). FIG. 7 illustrates the orientations of the viewing direction axes 40, 42, 44 of the optical channels 28, 30, 32 when the imaging scope 12 is in the second position. FIG. 8 illustrates the distal end of the imaging scope 12 when the imaging scope 12 is in a third position in which the imaging scope 12 has been rotated about its longitudinal axis 20 by two hundred forty degrees (240°) compared to the first position (see FIGS. 4 and 5). FIG. 9 illustrates the orientations of the viewing direction axes 40, 42, 44 of the optical channels 28, 30, 32 when the imaging scope 12 is in the third position.

In some embodiments, such as those in which the camera 16 is positioned in the housing 51 of the imaging scope 12, each of the at least three optical channels 28, 30, 32 further includes a respective image transmission device 72, 74, 76 (see FIG. 3) that transmits captured light from the respective objectives 34, 36, 38 of the optical channels 28, 30, 32 to the camera 16. Referring to FIG. 3, in the illustrated embodiment, each image transmission device 72, 74, 76 includes a rod lens, and each transmits the captured light therethrough in the form of a captured light beam having a circular cross-sectional shape. The image transmission devices 72, 74, 76 can additionally or alternatively include various different types of lenses or light conductors capable of transmitting the captured light from the objectives 34, 36, 38 to the proximal end portion of the imaging scope 12. The image transmission devices 72, 74, 76 can be configured to transmit the captured light therethrough in the form of a captured light beam having another cross-sectional shape that is at least partially circular (e.g., ovular, elliptical, etc.).

Figure 12:
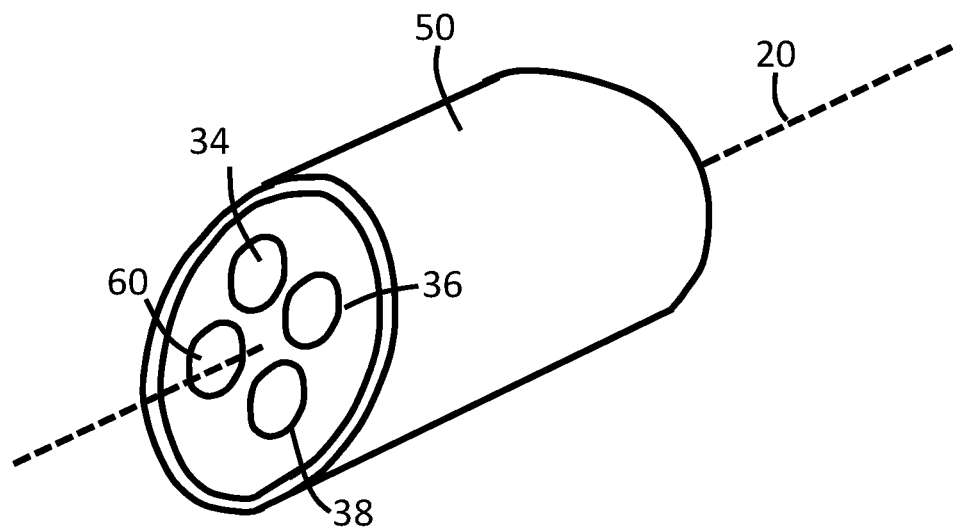
FIG. 12 schematically illustrates a distal end portion of an imaging scope having four (4) optical channels.
Figure 13:
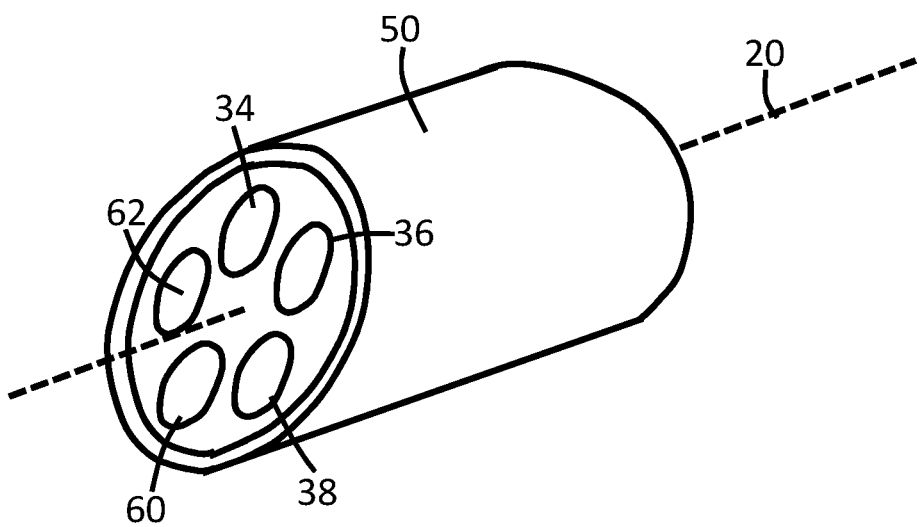
FIG. 13 schematically illustrates a distal end portion of an imaging scope having five (5) optical channels.
Figure 14:
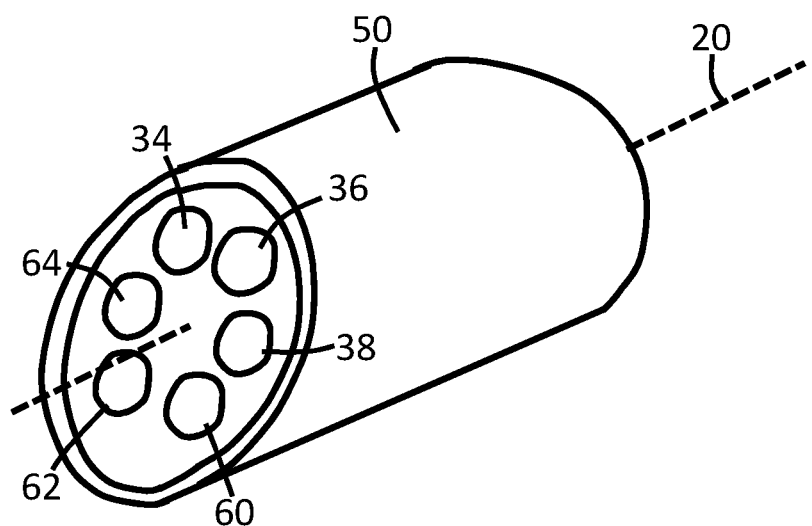
FIG. 14 schematically illustrates a distal end portion of an imaging scope having six (6) optical channels.

The number of optical channels 28, 30, 32 included in the imaging scope imaging scope 12 can vary. In the embodiments illustrated in FIGS. 1-11, the imaging scope 12 includes three (3) optical channels 28, 30, 32. In other embodiments, the imaging scope 12 can include four (4) optical channels (see FIG. 12 showing four (4) objectives 34, 36, 38, 60); five (5) optical channels (see FIG. 13 showing five (5) objectives 34, 36, 38, 60, 62); six (6) optical channels (see FIG. 14 showing six (6) objectives 34, 36, 38, 60, 62, 64), or more than six (6) optical channels. The greater the number of optical channels, the greater the number of rotational positions of the imaging scope 12 in which a pair of optical channels are parallel with a horizon plane 26.

Referring to FIGS. 2 and 3, in the illustrated embodiments, the imaging scope 12 further includes a plurality of light sources 66 positioned within the shaft channel 54 proximate the window 61. The light sources 66 are positioned radially between the optical channels 28, 30, 32 and the shaft wall 52. In other embodiments, the objectives 34, 36, 38 and the light sources 66 can be arranged in a different manner relative to one another, or in a different manner relative to the distal end portion of the imaging scope 12.

In the illustrated embodiments, the light sources 66 are connected to the controller 14 via wires 68, 70, and the controller 14 controls (e.g., activates, deactivates) the light sources 66 such that the light sources 66 selectively illuminate an object by selectively emitting illumination light through the window 61 and out of the distal end of the imaging scope 12. In some embodiments, the controller 14 is configured to selectively activate one or more light sources 66 depending on which optical channels 28, 30, 32 form the activated pair. In such embodiments, the controller 14 can be configured to continuously change which light sources 66 are activated in order to keep up with continuous changes to which optical channels 28, 30, 32 form the activated pair.

The camera 16 includes at least two image sensors 82, 84, 86 (e.g., charge-coupled devices (CODs), complementary metal-oxide semiconductors (CMOSs), etc.). Each of the image sensors 82, 84, 86 includes at least a portion of a light-sensitive surface configured to receive captured light from one of the optical channels 28, 30, 32 of the imaging scope 12, and each is configured to generate a 2D digital image representative of such captured light. Although the illustrated embodiments depict the image sensors 82, 84, 86 as being discrete components relative to one another, in other embodiments a single component could form more than one image sensor. For example, in some embodiments the light sensitive surface of a CCD or another imaging device could be subdivided into several predetermined portions, with each of the several predetermined portions forming a separate image sensor. In such embodiments, light received on a first predetermined portion of the light-sensitive surface of the CCD could be said to be received by a first image sensor, light received on a second predetermined portion of the light-sensitive surface of the CCD could be said to be received by a second image sensor, and so on. In the illustrated embodiments, the number of image sensors 82, 84, 86 is the same as the number of optical channels 28, 30, 32 of the imaging scope 12. In other embodiments, the camera 16 includes only two (2) image sensors, or another number of image sensors that is fewer than the number of optical channels 28, 30, 32 of the imaging scope 12.

In some embodiments, such as those in which the number of image sensors 82, 84, 86 is the same as the number of optical channels 28, 30, 32, the image sensors 82, 84, 86 can be positionally fixed relative to the optical channels 28, 30, 32 during operation of the imaging system 10. In such embodiments, each of the optical channels 28, 30, 32 can be permanently paired with a respective image sensor 82, 84, 86. In other embodiments, such as those in which the camera 16 includes only two (2) image sensors, the image sensors can be rotatable relative to the optical channels 28, 30, 32 during operation of the imaging system 10. In such embodiments, a parallel alignment of the two (2) image sensors relative to the horizon plane 26 remains fixed during operation of the imaging system 10 (i.e., even during rotation of the imaging scope 12 about its longitudinal axis 20 relative to the horizon plane 26).

In the illustrated embodiments, the camera 16 is a video camera, and thus the 2D digital images generated by the image sensors 82, 84, 86 can represent one of a plurality of time-sequenced frames of a digital video.

Referring to FIG. 2, in the illustrated embodiments, the controller 14 (e.g., a camera control unit (CCU)) is in signal communication with the camera 16 (in particular, the image sensors 82, 84, 86 of the camera 16). As described above, the controller 14 is configured to activate a pair of optical channels that is at least as parallel relative to the horizon plane 26 as any other pair of optical channels among the at least three optical channels 28, 30, 32. The term "activate," and variations thereof, is used herein to describe the process by which the controller 14 causes particular optical channels to be those from which captured light is used by the camera 16 to generate the 2D digital images. That is, light captured and transmitted through an activated optical channel 28, 30, 32 is subsequently received by the light-sensitive surface of an image sensor 82, 84, 86 of the camera 16, and the respective image sensor 82, 84, 86 generates a 2D digital image representative thereof. In contrast, light captured and transmitted through an optical channel 28, 30, 32 that has not been activated by the controller 14 (hereinafter an "inactive" optical channel 28, 30, 32) will not be received by an image sensor 82, 84, 86 of the camera 16. Alternatively, if such light is received by an image sensor 82, 84, 86, the image sensor 82, 84, 86 will not generate a 2D digital image representative thereof, or it will generate a 2D digital image that will not be used to generate a 3D digital image.

The controller 14 can automatically activate or deactivate a pair of optical channels in various different ways. In embodiments in which the number of image sensors 82, 84, 86 included in the camera 16 is the same as the number of optical channels 28, 30, 32 of the imaging scope 12 (see FIG. 2), the controller 14 can activate a particular optical channel 28, 30, 32, for example, by instructing a corresponding image sensor 82, 84, 86 of the camera 16 to generate a 2D digital image representative of the light received from the particular optical channel 28, 30, 32. In other embodiments in which the camera 16 includes only two (2) image sensors and the image sensors are rotatable relative to the optical channels 28, 30, 32 as described above, the controller 14 can activate a particular pair of optical channels 28, 30, 32, for example, by sending instructions to the camera 16 that causes movement of the image sensors relative to the optical channels 28, 30, 32 (e.g., via actuation of the image sensors) until the image sensors are aligned with (i.e., positioned to receive light from) the particular pair of optical channels 28, 30, 32.

Figure 10:
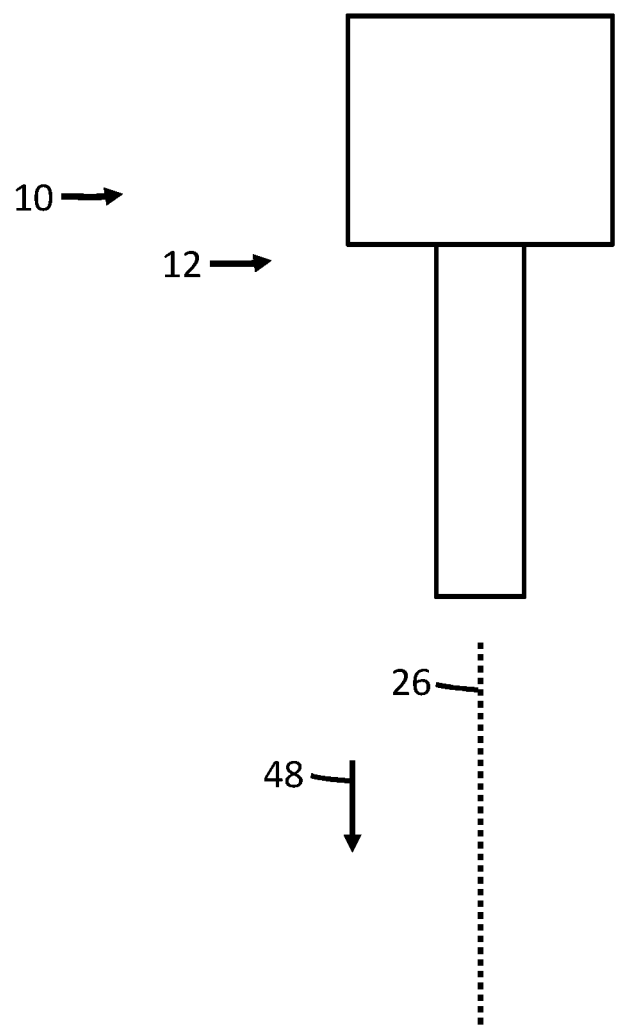
FIG. 10 schematically illustrates the imaging system of FIG. 1 arranged such that the horizon plane is parallel to a gravity vector.

In the illustrated embodiments, the imaging system 10 further includes a gravity sensor 88 (see FIGS. 2 and 11) that sends a data signal to the controller 14 regarding the orientation and/or movement of the imaging scope 12 relative to the direction of a gravity vector 48, and the controller 14 uses such data to activate a pair of optical channels accordingly. The horizon plane 26 can thus be chosen and/or determined by the controller 14 based on the data signal received from the gravity sensor 88. In the illustrated embodiments, the gravity sensor 88 is positioned within the housing 51 of the imaging scope 12. In other embodiments, the gravity sensor 88 could be positioned within the shaft 50 of the imaging scope 12, or in another location where the gravity sensor 88 will be rotated together with the imaging scope 12 and/or the optical channels 28, 30, 32 thereof. The gravity sensor 88 can be in the form of a three-axis acceleration sensor, or in the form of another known device that is capable of performing the functionality described herein. In some embodiments, the gravity sensor 88 can be turned off manually and the orientation of the horizon plane 26 can be selectively chosen and adjusted by a user as described above. In some embodiments, additional sensors like magnetometers and gyroscopes can be used to improve or correct the measurement of such a gravity sensor 88, as is known in the prior art. Additional information may be needed, for example, when the imaging scope 12 is held so that the longitudinal axis 20 of the imaging scope 12 is parallel to the direction of a gravity vector 48, as shown in FIG. 10. When the imaging scope 12 is held in such a position, the gravity sensor 88 may not be able to detect the movement of the imaging scope 12 relative to the gravity vector 48 without information from additional sensors (e.g., magnetometers, gyroscopes, etc.).

In some embodiments, the controller 14 is also configured to perform known digital image erecting and digital flip-mirror functions on the 2D digital images before transmitting the same to the 3D processor 18.

The functionality of the controller 14 can be implemented using mechanical, analog and/or digital hardware (e.g., counters, switches, logic devices, memory devices, programmable processors, non-transitory computer-readable storage mediums), software, firmware, or a combination thereof. The controller 14 can perform one or more of the functions described herein by executing software, which can be stored, for example, in a memory device. A person having ordinary skill in the art would be able to adapt (e.g., construct, program) the controller 14 to perform the functionality described herein without undue experimentation.

The 3D processor 18 is in signal communication with the controller 14, and receives the 2D digital images from the controller 14 and processes the 2D digital images in a known manner to generate a 3D digital image. In some embodiments, the 3D processor 18 is further configured to calculate a depth map (not shown) using the 2D digital images. Such a depth map provides a calculation of the relative distances from the window 61 at the distal end of the imaging scope 12 to various objects across the field of view of the imaging scope 12. The parallax between the 2D digital images allows the 3D processor to calculate such a depth map.

The functionality of the 3D processor 18 can be implemented using analog and/or digital hardware (e.g., counters, switches, logic devices, memory devices, programmable processors, non-transitory computer-readable storage mediums), software, firmware, or a combination thereof. The 3D processor 18 can perform one or more of the functions described herein by executing software, which can be stored, for example, in a memory device. A person having ordinary skill in the art would be able to adapt (e.g., construct, program) the 3D processor 18 to perform the functionality described herein without undue experimentation.

Another aspect of the invention involves a method that includes the steps of: (i) providing an imaging scope 12 that extends along a longitudinal axis 20 between a proximal end portion and a distal end portion thereof, the imaging scope 12 having at least three optical channels 28, 30, 32, each including a respective objective 34, 36, 38 positioned at the distal end portion of the imaging scope 12 and configured to capture light reflected from an object, the objectives 34, 36, 38 being annularly-spaced relative to one another and positioned such that respective viewing direction axes 40, 42, 44 of the at least three optical channels 28, 30, 32 extend at least substantially parallel to one another; (ii) rotating the imaging scope 12 about the longitudinal axis 20 relative to a horizon plane 26; (iii) activating, among the at least three optical channels 28, 30, 32, a pair of optical channels that is at least as parallel relative to the horizon plane 26 as any other pair of optical channels among the at least three optical channels 28, 30, 32; (iv) generating a first 2D digital image representative of light captured by a first optical channel of the activated pair of optical channels, and a second 2D digital image representative of light captured by a second optical channel of the activated pair of optical channels; (v) generating a 3D digital image using the first 2D digital image and the second 2D digital image.

The present disclosure describes aspects of the invention with reference to the exemplary embodiments illustrated in the drawings; however, aspects of the invention are not limited to the exemplary embodiments illustrated in the drawings. It will be apparent to those of ordinary skill in the art that aspects of the invention include many more embodiments. Accordingly, aspects of the invention are not to be restricted in light of the exemplary embodiments illustrated in the drawings. It will also be apparent to those of ordinary skill in the art that variations and modifications can be made without departing from the true scope of the present disclosure. For example, in some instances, one or more features disclosed in connection with one embodiment can be used alone or in combination with one or more features of one or more other embodiments.

What is claimed is:

1. An imaging system, comprising:
   an imaging scope extending along a longitudinal axis between a proximal end portion and a distal end portion thereof, the imaging scope selectively rotatable about the longitudinal axis relative to a horizon plane, the imaging scope having at least three optical channels, each including a respective objective positioned at the distal end portion of the imaging scope, and each configured to capture light reflected from an object, the objectives of the at least three optical channels being annularly-spaced relative to one another and positioned such that respective viewing direction axes of the at least three optical channels extend at least substantially parallel to one another;

a controller configured to activate, among the at least three optical channels, a pair of optical channels that is at least as parallel relative to the horizon plane as any other pair of optical channels among the at least three optical channels;

a camera configured to generate a first 2D digital image representative of light captured by a first optical channel of the activated pair of optical channels, and a second 2D digital image representative of light captured by a second optical channel of the activated pair of optical channels; and a 3D processor configured to generate a 3D digital image using the first 2D digital image and the second 2D digital image.

2. The imaging system of claim 1, wherein the pair of optical channels defines a viewing horizon line that is at least as parallel relative to the horizon plane as that of any other pair of optical channels among the at least three optical channels, the viewing horizon line being a line that extends perpendicularly between the respective viewing direction axes of the pair of optical channels.

3. The imaging system of claim 2, wherein the horizon plane is oriented perpendicular relative to a gravity vector.

4. The imaging system of claim 2, wherein the horizon plane is oriented parallel relative to a gravity vector.

5. The imaging system of claim 2, wherein the horizon plane is non-perpendicularly offset relative to a gravity vector.

6. The imaging system of claim 2, wherein an orientation of the horizon plane is selectively chosen by a user.

7. The imaging system of claim 2, wherein the horizon plane is determined by the controller based on a data signal received from a gravity sensor, the data signal including data regarding an orientation and/or movement of the imaging scope relative to a direction of a gravity vector.

8. The imaging system of claim 1, wherein the controller is configured such that, during activation of the pair of optical channels, the controller causes first and second optical channels of the at least three optical channels to be those from which captured light is used by the camera to generate the 2D digital images.

9. The imaging system of claim 1, wherein light captured and transmitted through a first optical channel of the pair of optical channels is subsequently received by a light-sensitive surface of a first image sensor of the camera, and the first image sensor generates the first 2D digital image representative thereof; and wherein light captured and transmitted through a second optical channel of the pair of optical channels is subsequently received by a light-sensitive surface of a second image sensor of the camera, and the second image sensor generates the second 2D digital image representative thereof.

10. The imaging system of claim 1, wherein the controller is configured to activate the pair of optical channels by instructing corresponding image sensors of the camera to generate respective 2D digital images representative of light received from first and second optical channels of the pair of optical channels.

11. The imaging system of claim 1, wherein the controller is configured to activate the pair of optical channels by moving image sensors of the camera relative to the pair of optical channels until the image sensors are aligned with the pair of optical channels.

12. The imaging system of claim 1, wherein the imaging scope further includes:
a shaft that extends in a direction of the longitudinal axis of the imaging scope, the shaft being rigid, and the shaft including a tubular shaft wall and a shaft channel defined by an inner surface of the shaft wall; and
a housing connected to a proximal end portion of the shaft.

13. The imaging system of claim 12, wherein the imaging scope further includes a window disposed at the distal end portion of the shaft, the window being at least substantially transparent.

14. The imaging system of claim 12, wherein the housing houses the camera; and
wherein each of the at least three optical channels includes a respective image transmission device that transmits captured light from the respective objectives of the at least three optical channels to the camera.

15. The imaging system of claim 12, wherein the camera is housed in a distal end portion of the shaft.

16. The imaging system of claim 12, wherein at least one of the camera, the controller, and the 3D processor are remotely positioned relative to the imaging scope.

17. The imaging system of claim 1, wherein the respective viewing direction axes of the at least three optical channels are angularly offset relative to the longitudinal axis of the imaging scope.

18. The imaging system of claim 1, wherein the camera includes at least two image sensors, each of the at least two image sensors including at least a portion of a light-sensitive surface configured to receive captured light from one of the at least three optical channels, and configured to generate 2D digital images representative of such captured light.

19. The imaging system of claim 18, wherein a number of image sensors included in the camera is the same as a number of optical channels.

20. The imaging system of claim 18, wherein the at least two image sensors are positionally fixed relative to the at least three optical channels.

21. The imaging system of claim 18, wherein the camera includes a number of image sensors that is fewer than the number of optical channels.

22. The imaging system of claim 21, wherein the at least two image sensors are rotatable relative to the at least three optical channels so that a parallel alignment of the image sensors relative to the horizon plane remains fixed during operation of the imaging system.

23. The imaging system of claim 22, wherein respective rotational positions of the at least two image sensors relative to the at least three optical channels are controlled by the controller.

24. The imaging system of claim 1, wherein the respective viewing direction axes of the at least three optical channels each have a fixed angular offset relative to the longitudinal axis of the imaging scope.

25. An imaging system, comprising:
an imaging scope extending along a longitudinal axis between a proximal end portion and a distal end portion thereof, the imaging scope selectively rotatable about the longitudinal axis relative to a horizon plane, the imaging scope having at least three optical channels, each including a respective objective positioned at the distal end portion of the imaging scope, and each configured to capture light reflected from an object, the objectives of the at least three optical channels being annularly-spaced relative to one another and positioned such that respective viewing direction axes of the at least three optical channels extend at least substantially parallel to one another;
- a controller configured to activate, among the at least three optical channels, a pair of optical channels defining a viewing horizon line that is at least as parallel relative to the horizon plane as that of any other pair of optical channels among the at least three optical channels, the viewing horizon line being a line that extends perpendicularly between the respective viewing direction axes of the pair of optical channels;
- a camera configured to generate a first 2D digital image representative of light captured by a first optical channel of the activated pair of optical channels, and a second 2D digital image representative of light captured by a second optical channel of the activated pair of optical channels; and
- a 3D processor configured to generate a 3D digital image using the first 2D digital image and the second 2D digital image.

26. A method, comprising:
providing an imaging scope that extends along a longitudinal axis between a proximal end portion and a distal end portion thereof, the imaging scope having at least three optical channels, each including a respective objective positioned at the distal end portion of the imaging scope, and each configured to capture light reflected from an object, the objectives being annularly-spaced relative to one another and positioned such that respective viewing direction axes of the at least three optical channels extend at least substantially parallel to one another;
rotating the imaging scope about the longitudinal axis relative to a horizon plane;
activating, among the at least three optical channels, a pair of optical channels that is at least as parallel relative to the horizon plane as any other pair of optical channels among the at least three optical channels;
generating a first 2D digital image representative of light captured by a first optical channel of the activated pair of optical channels, and a second 2D digital image representative of light captured by a second optical channel of the activated pair of optical channels; and
generating a 3D digital image using the first 2D digital image and the second 2D digital image.

* * * * *